United States Patent
Jin et al.

(10) Patent No.: US 8,691,955 B2
(45) Date of Patent: Apr. 8, 2014

(54) USE OF α1G SUBUNIT OF T-TYPE CALCIUM CHANNEL AS DIAGNOSTIC MARKER FOR PREGNANCY IN CATTLE

(75) Inventors: Dong Il Jin, Daejeon (KR); Rong Xun Han, Daejeon (KR); Hong Rye Kim, Seoul (KR)

(73) Assignee: The Industry & Academic Cooperation in Chungnam National University, Daejeon (KR)

( * ) Notice: Subject to any disclaimer, the term of this patent is extended or adjusted under 35 U.S.C. 154(b) by 0 days.

(21) Appl. No.: 13/290,894

(22) Filed: Nov. 7, 2011

(65) Prior Publication Data
US 2012/0329055 A1    Dec. 27, 2012

(30) Foreign Application Priority Data

Jun. 24, 2011    (KR) .................. 10-2011-0061779

(51) Int. Cl.
*A61K 39/395*    (2006.01)
*C07K 16/28*    (2006.01)

(52) U.S. Cl.
USPC ................................... 530/387.9; 424/139.1

(58) Field of Classification Search
None
See application file for complete search history.

(56) References Cited

U.S. PATENT DOCUMENTS 6,534,634 B1    3/2003    Ivell

FOREIGN PATENT DOCUMENTS

| KR | 1020000065910 A | 11/2000 |
|----|----|----|
| KR | 1020090049917 A | 5/2009 |

OTHER PUBLICATIONS

Schrier et al., Am J Physiol Cell Physiol 280:C265-C272, 2001.*
Andreasen et al., Am J Physiol Renal Physiol 279:F997-F1005, 2000.*
Genbank Accession No. AF236639, Bos taurus alpha1G T-type calcium channel subunit, available Nov. 29, 2001 and accessed Feb. 5, 2013.*

* cited by examiner

*Primary Examiner* — Marianne P Allen
(74) *Attorney, Agent, or Firm* — Joseph H. Kim; JHK Law (57) ABSTRACT

The present invention relates to a marker composition for pregnancy diagnosis in cattle, a pregnancy diagnosis composition, and a pregnancy diagnosis method, which use a pregnancy-specific protein in cattle. The present inventors discovered an α1G subunit protein of the T-type calcium channel expressed specifically in pregnant cows, and produced a specific antibody against this protein. Therefore, the present invention has the effect of detecting pregnancy in cows easily, quickly, and accurately early in the pregnancy.

1 Claim, 5 Drawing Sheets

USE OF α1G SUBUNIT OF T-TYPE CALCIUM CHANNEL AS DIAGNOSTIC MARKER FOR PREGNANCY IN CATTLE

CROSS-REFERENCE PARAGRAPH

This application claims the benefit of priority to Korean Patent Application No. 10-2011-0061779, filed on Jun. 24, 2011, the contents of which are incorporated by reference herein in its entirety.

TECHNICAL FIELD

The present invention relates to a novel marker composition for pregnancy diagnosis in cattle, which can effectively diagnose and predict pregnancy in cattle at an early stage, a pregnancy diagnostic composition, and a method for diagnosing pregnancy in cattle using the composition.

BACKGROUND ART

Pregnancy diagnosis in dairy cattle enables planned breeding in dairy management, and allows early detection and treatment of reproductive disorders, and it is important to perform the diagnosis at an early stage of pregnancy in order to improve the conception rate after intrauterine insemination and prevent infertility. As a result of the diagnosis, if pregnancy is detected, adequate care during pregnancy and a hygienic conditions will be provided to prevent abortion early in the pregnancy and help cows to give birth to healthy calves. Otherwise, if pregnancy is not detected, the cause of non-pregnancy should be found to take proper actions, and intrauterine insemination (Artificial insemination) may be tried as soon as possible to increase the reproductive efficiency of the cows. Accordingly, dairy cattle pregnancy should be diagnosed at an early stage of pregnancy if possible. Moreover, the diagnosis should not affect pregnant cattle and their fetuses, the diagnostic method should be easy to perform at low cost and livestock farms should be easy to perform this technology.

Pregnancy diagnosis in cattle methods currently in use include rectoscopy, ultrasonic diagnosis, and a pregnancy diagnosis method using a diagnostic kit that uses changes in hormone concentration in blood.

The rectoscopy is a method for detecting pregnancy by observing changes in reproductive organs, for example, womb size, waving feeling, position, fetal membranes, corpus luteum, fetus, placental growth stimulation, or uterine artery hypertrophy, through rectal examination. The ultrasonic pregnancy diagnosis, as a rule, uses a linear type probe of 5.0 MHz or 7.5 MHz attached to an ultrasonic diagnostic apparatus. With this method, a round or elliptical embryo sac that appears to be black can be observed in the uterine horn around 22 days of pregnancy. However, it is desirable to perform diagnosis after 27 days of pregnancy. Amniotic fluid appearing to be black is observed in the uterine horn around 30 days of pregnancy, and the fetus looks like a white processus. It is possible to estimate how many days old the fetus by measuring the length of the fetus and the size of each structure, and it is also possible to identify the sex of the fetus by detecting the positions of reproductive organics between 60 and 120 days of pregnancy. The risk of miscarriage is very low because the test is done by moving the probe over the womb without pulling the womb.

The pregnancy diagnostic kit using changes in hormone concentration in blood was developed with the focus on the fact that the progesterone concentration in the blood or milk from nonpregnant cows is lower than that of pregnant cows. If a cow is pregnant, the corpus luteum grows into persistent corpus luteum and is involved in the maintenance of the pregnancy. Therefore, pregnant cows have a higher level of progesterone (above 3 to 4 ng/ml) than nonpregnant cows (1 ng/ml or so) due to the effects of progesterone released from the persistent corpus luteum.

The rectoscopy may be used for diagnosis after 30 to 40 days of pregnancy. As the diagnostic accuracy varies according to the degree of training of vets, a proper time for diagnosis should be chosen according to the degree of skillfulness of vets. Moreover, a report showed that 10% of fetuses from cattle were stillborn due to early absorption before 150 days of pregnancy when the diagnosis using rectoscopy had been performed around 35 to 41 days of pregnancy, and 8% of cattle, on average, on which an early pregnancy diagnosis was performed by rectoscopy miscarried around 60 days of pregnancy. This reveals the drawback that the sooner the pregnancy diagnosis is made, the higher the risk of early death of fetuses.

In the ultrasonic pregnancy diagnosis, amniotic fluid and a fetus can be seen directly through the screen of an apparatus. Thus, it is an accurate pregnancy diagnosis method, but limitations on the use of this method in livestock farms because an expensive ultrasonic diagnostic apparatus are required.

In the pregnancy diagnosis using a diagnostic kit, the accuracy is not more than 70 to 80%; the reason of which is, because cows show high levels of progesterone if they have reproductive disorders caused by ovarian diseases or uterine diseases, resulting in a high rate of misidentification.

Currently, a number of pregnancy-associated proteins from livestock have been reported: equine chorionic gonadotropin (ECG) is used for pregnancy diagnosis in horses, bovine placental lactogen (bPL), pregnancy specific protein-B (PSPB), pregnancy serum protein-60 (PSP-60) and bovine pregnancy-associated glycoprotein (bPAG) are used for pregnancy diagnosis in cattle, and progesterone in milk or serum is also used. However, in the case of pregnancy diagnosis using the pregnancy-associated proteins and progesterone, the misidentification rate of negative and positive specimen is relatively high, and hence the accuracy of a pregnancy test is not high, thus leading to low practicability. Consequently, there is a need for the development of a new method for making accurate diagnosis of cattle pregnancy more easily and quickly at an early stage.

DISCLOSURE

Technical Problem

Therefore, the present inventors have developed a method for diagnosing pregnancy in cattle using α1G gene and protein upon discovering an α1G subunit of the T-type calcium channel is expressed specifically in the milk of cows throughout all stages of pregnancy including an early stage of the pregnancy while conducting a study on specific proteins in the milk of pregnant cows by second-dimensional electrophoresis (2-D) to find proteins expressed in the milk of cows specifically to pregnancy at an early stage of pregnancy, the specific proteins being detected by comparative analysis of milk proteins from pregnant and nonpregnant cows using proteomic technologies.

Accordingly, it is an object of the present invention to provide a marker composition for pregnancy diagnosis in cattle, the marker composition including an α1G subunit gene of the T-type calcium channel or an α1G subunit protein of the T-type calcium channel encoded from the gene.

It is another object of the present invention to provide a marker composition for pregnancy diagnosis in cattle, the marker composition including a substance for measuring the expression level of mRNA of an α1G subunit gene of the T-type calcium channel or the expression level of a protein encoded from the gene.

It is a yet another object of the present invention to provide a method for diagnosing pregnancy in cattle by detecting the expression of α1G gene using a substance for measuring the level of mRNA of an α1G subunit gene of the T-type calcium channel or the level of a protein encoded from the gene.

It is a further object of the present invention to provide a kit for pregnancy diagnosis in cattle, including the pregnancy diagnostic marker.

Technical Solution

To accomplish the aforementioned objects of the present invention, there is provided a marker composition for pregnancy diagnosis in cattle, the marker composition including an α1G subunit gene of the T-type calcium channel or an α1G protein encoded from the gene.

The present invention provides a composition for pregnancy diagnosis in cattle, the composition including a substance for measuring the level of mRNA of an α1G subunit gene of the T-type calcium channel or the level of an α1G protein encoded from the gene.

In one embodiment of the present invention, the α1G protein may have an amino acid sequence of SEQ NO. ID: 1.

In one embodiment of the present invention, the substance for measuring the level of mRNA of the α1G gene may be a primer or probe capable of amplifying the α1G gene or its mRNA, and the substance for measuring the level of the α1G protein may be an antibody that specifically recognizes the α1G protein.

In one embodiment of the present invention, the antibody may comprise an amino acid sequence of SEQ NO. ID: 2.

Further, the present invention provides a method for diagnosing pregnancy in cattle comprising detecting the level of expression of an α1G gene in the biological sample from a cow, wherein expression of an α1G gene is indicative of pregnancy of cow.

In one embodiment of the present invention, the expression of the α1G gene may be detected using cows' milk, tissues, cells, whole blood, serum, plasma, saliva, or urine.

In one embodiment of the present invention, the level of expression of the α1G gene is detected using a substance for measuring the level of mRNA of an α1G gene of the T-type calcium channel or the level of an α1G protein encoded from the gene.

In one embodiment of the present invention, the substance for measuring the level of mRNA of the α1G gene may be a primer or probe capable of specifically binding to the α1G gene, and the substance for measuring the level of the α1G protein may be an antibody that specifically recognizes the α1G protein.

In one embodiment of the present invention, the antibody may comprise amino acid sequence of SEQ NO. ID: 2.

In one embodiment of the present invention, the measurement may be carried out using a method selected from the group consisting of reverse transcriptase-polymerase chain reaction, real time reverse transcriptase-polymerase chain reaction, Western blot, Northern blot, enzyme linked immunosorbent assay (ELISA), radioimmunoassay (RIA), radioimmunodiffusion, immunoprecipitation assay, and immunohistochemical analysis.

Further, the present invention provides a kit for pregnancy diagnosis in cattle, including the composition for pregnancy diagnosis in cattle.

In one embodiment of the present invention, the kit may be a PCR kit, a DNA chip kit, or a protein chip kit.

Furthermore, the present invention provides a microarray for pregnancy diagnosis in cattle, including the composition for pregnancy diagnosis in cattle.

Advantageous Effects

The present invention relates to a marker composition for pregnancy diagnosis in cattle, a pregnancy diagnosis composition, and a pregnancy diagnosis method, which use an α1G subunit gene of the T-type calcium channel or an α1G protein encoded from the gene, and has the effect of diagnosing pregnancy in cattle early in the pregnancy easily, quickly, and accurately. If the detection of pregnancy of a cow having an estrous cycle of 21 days is available before 20 days after intrauterine insemination or mating (copulation), intrauterine insemination can be done when the next mating season (estrus) when pregnancy is not detected, thereby significantly shortening non-pregnancy periods for cows. The present invention allows pregnancy diagnosis in cows from the 18th day after insemination and therefore determines whether a cow is pregnant early in the pregnancy. Hence, non-pregnancy periods for cows can be shortened, and the cost and time of pregnancy diagnosis can be reduced, thereby relieving economic burden on stock farmers, and ultimately the reproductive efficiency can be increased, thereby facilitating the development of livestock industry.

DESCRIPTION OF DRAWINGS

The above and other objects and features of the present invention will become apparent from the following description of the preferred embodiments given in conjunction with the accompanying drawings, in which.

BEST MODE FOR THE INVENTION

The present invention is characterized in that it provides a marker composition for pregnancy diagnosis in cattle, the marker composition including an alphalG (α1G) gene, which is a subunit of the T-type calcium channel, or an α1G protein encoded therefrom.

Pregnancy diagnosis in cattle should be done at an early stage of pregnancy if possible. Moreover, the diagnosis should not affect pregnant cattle and their fetuses, the diagnostic operation should be easily performed at low cost and it should be easy for farms to employ this technique.

Conventionally, a number of pregnancy-associated proteins from livestock have been reported: however, in the case of conventional pregnancy diagnosis using the pregnancy-associated proteins, the accuracy for negative and positive specimen is not high, thus leading to low practicability.

Accordingly, if there are developed technologies which allow accurate diagnosis of pregnancy before 20 days after intrauterine insemination or mating (copulation) in cow having an estrous cycle of 21 days, intrauterine insemination can be done when the next estrus (rutting season). Hence, non-pregnancy periods for cows can be significantly shortened, and the reproductive efficiency can be increased, leading to economic and time gains.

Accordingly, the present inventors found an α1G T-type calcium channel subunit (α1G), which is a protein specifically expressed in the milk of pregnant cows, by proteomic analysis, and produced a polyclonal antibody by synthesizing 15 amino acid regions with high antigenicity of the amino acid sequence of the α1G protein and immunizing the synthesized amino acids into rabbits. As a result of performing Western blot of milk from nonpregnant and pregnant cows with the produced antibody, it was found that an α1G subunit of the T-type calcium channel was expressed specifically to pregnancy.

The T-type calcium channel is a type of voltage-gated calcium channel. "T" stands for transient referring to the length of activation. The T-type calcium channel is characterized by low-threshold activation.

As with other sub-types of voltage-gated calcium channel, the α1 subunit is the one that determines most of the channel's properties. T-type calcium channels may contain three α1 subunits, α1G (Cav3.1), α1H (Cav3.2) and α1I (Cav3.3) (Perez-Reyes, E. et al. (1998) Molecular characterization of a neuronal low-voltage-activated T-type calcium channel, Nature 391 (6670), 896-900).

The alpha 1G subunit (α1G subunit) of the T-type calcium channel, also known as CACNA1G or Cav3.1, is a protein which in humans is encoded by the CACNA1G gene. α1G is distributed in many tissues, and contributes to the control of the influx of calcium ions and the depolarization. α1G responds to changes in membrane potential, and, in particular, is thought to produce a steady influx of calcium ions near the resting membrane potential (Cueni et al., 2009, Ca signaling by T type Ca channels in neurons, Pfluger Arch, 457 (5), 1161-1172). Abnormal expression of the T-type channel related to α1G appears to be involved in epilepsy, arrhythmia, sleep disorders, and abnormal gain of weight (Anderson et al., 2005, Thalamic Cav3.1 T-type Ca channel plays a crucial role in stabilizing sleep, Proc Natl Acad SciUSA, 102(5), 1743-1748). Little is known about the function and structure of the α1G subunit.

The present inventors have completed the present invention upon finding that the alphalG (α1G) subunit of the T-type calcium channel is highly expressed specifically in pregnant cows.

According to one embodiment of the present invention, the present inventors found, by two-dimensional electrophoresis protein, spots expressed specifically in pregnant cows, wherein spots consistently expressed in each of samples were detected repeatedly, protein spots showing differences in expression specifically between the milk of pregnant cows and the milk of nonpregnant cows (see FIGS. 1a and 1b), and, in particular, the α1G subunit of the T-type calcium channel expressed specifically in the pregnant cows was identified (see Example 1).

Moreover, in order to produce an antibody specifically binding to the α1G protein identified specifically to pregnancy in cows' milk, according to one embodiment of the present invention, the present inventors analyzed the amino acid sequence (Sequence List 1) of the α1G protein having specificity to select amino acids with hydrophilic property, high surface exposure, and high probability of antigenicity and synthesize a peptide having a sequence of 15 amino acids (Sequence List 2). This peptide was immunized in rabbits for a total of three boosts to generate an antibody (see Example 2).

To determine whether the antibody according to the present invention has α1G protein specificity, according to one embodiment of the present invention, the expression or non-expression of the α1G protein was analyzed by performing Western blot of milk samples from cows of a control group and pregnant cows of an experimental group with the produced antibody. As a result, strong expression of the α1G protein was observed using the antibody produced by the present inventors.

Moreover, the present inventors performed Western blot of milk samples for each stage of pregnancy using the α1G antibody. This revealed that the expression of the α1G protein was observed from the 18th day of pregnancy, which is an early stage of pregnancy, and the expression level was the highest around 20 days of pregnancy and tends to decrease slightly in the middle and later stages of pregnancy. Although there are differences in expression level between each stage, it can be seen that α1G protein expression tends to increase remarkably throughout all stages of pregnancy (see Example 3).

Therefore, the present inventors concluded through these results that the diagnostic composition and method of the present invention can detect pregnancy in cattle at almost all stages of pregnancy by using the alphalG (α1G) subunit of the T-type calcium channel, and, in particular, can be used as an excellent pregnancy diagnostic marker and method which is capable of detecting pregnancy even at an early stage of pregnancy when it is hard to diagnose pregnancy by conventional methods.

Accordingly, the present invention provides a marker composition for pregnancy diagnosis in cattle, the marker composition including an alphalG (α1G) gene of the T-type calcium channel or an α1G protein encoded therefrom.

The term "pregnancy diagnostic marker", as used herein, is intended to indicate a substance capable of diagnosing pregnancy by distinguishing pregnant individuals from nonpregnant individuals, and includes organic biological molecules, quantities of which are increased or decreased in biological sample of pregnant individuals relative to nonpregnant individuals, such as polypeptides, nucleic acids (e.g., mRNA, etc.), lipids, glycolipids, glycoproteins and sugars (monosaccharides, disaccharides, oligosaccharides, etc.). The marker for pregnancy in cattle provided in the present invention is alphalG (α1G) gene or protein, which is a subunit of the T-type calcium channel, whose expression level is increased in biological samples from pregnant individuals: preferably, the α1G protein have amino acid sequences represented by SEQ ID NO:1.

Moreover, the present invention provides a composition for pregnancy diagnosis in cattle, the composition including a substance for measuring the level of an α1G subunit gene of the T-type calcium channel or the level of an α1G protein encoded from the gene. More preferably, the present invention provides a composition for pregnancy diagnosis in cattle, the composition including a substance for measuring the level of mRNA of an α1G subunit gene of the T-type calcium channel or the level of an α1G protein encoded from the gene.

That is, in the present invention, the level of the α1G gene indicates the expression of the gene, preferably, the mRNA level of expression of the α1G gene, i.e., the amount of mRNA expression. Substances for measuring the level of expression of the gene include all known substances which can be used; preferably, a primer or probe specific to the α1G gene. In the present invention, the α1G gene-specific primer or probe capable of amplifying all or a portion of the α1G gene can be designed by methods known in the art.

As used herein, the term "primer" refers to a single-strand oligonucleotide capable of initiating a template-directed DNA synthesis in an appropriate buffer under an appropriate condition (for example, in the presence of four different nucleoside triphosphates and polymerase) at a proper temperature. The appropriate length of the primer may vary according to various factors, for example, temperature and the purpose of use. The primer sequence does not necessarily need to be completely complementary to a part of the sequence of the template, but should be sufficiently complementary to be hybridized with the template and perform the unique function of the primers.

Accordingly, the primer of the invention does not necessarily need to be completely complementary to the nucleotide sequence of the α1G gene serving as the template, but should be sufficiently complementary to be hybridized with this gene sequence and perform the primer function. Preferably, the primer according to the present invention is used for gene amplification.

The term "amplification" or "amplifying" refers to a reaction in which nucleic acid molecules are amplified. Such gene amplifications are well known in the art. Examples are polymerase chain reaction (PCR), reverse-transcription polymerase chain reaction (RT-PCR), ligase chain reaction (LCR), transcription mediated amplification (TMA), nucleic acid based sequence amplification (NASBA) and so on.

As used herein, the term "probe" refers to a linear oligomer of natural or modified monomers or linkages, including deoxyribonucleotides and ribonucleotides, which is capable of specifically hybridized with a target nucleotide sequence, and occurring naturally or produced synthetically. The probe according to the present invention may be present in a single-strand form. Preferably, the probe is an oligodeoxyribonucleotide.

The probe of this invention can include naturally occurring dNMP (i.e., dAMP, dGMP, dCMP and dTMP), nucleotide analogs, or nucleotide derivatives. The probe of this invention can also include ribonucleotides. For example, the probe of this invention may include nucleotides with backbone modifications such as peptide nucleic acid (PNA) (M. Egholm et al., Nature, 365:566-568 (1993)), phosphorothioate DNA, phosphorodithioate DNA, phosphoramidate DNA, amide-linked DNA, MMI-linked DNA, 2'-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine, and diaminopurine.

Further, as used herein, the substance for measuring the α1G protein level may include monoclonal antibodies, polyclonal antibodies, and recombinant antibodies which specifically bind to the α1G protein.

In addition, as used herein, as the α1G protein was identified as a marker protein for diagnosing pregnancy as described above, a method of producing an antibody using the aforementioned protein can be easily carried out by techniques generally known to those skilled in the art. The production of antibodies, for example, polyclonal antibodies, may be carried out using a method widely known in the art, which includes injecting the α1G antigen into an animal and collecting blood samples from the animal to obtain sera containing antibodies. Such polyclonal antibodies may be prepared from a certain animal host, such as goats, rabbits, sheep, monkeys, horses, pigs, cows and dogs. Monoclonal antibodies may be prepared by a method widely known in the art, such as a hybridoma method (Kohler and Milstein (1976) European Journal of Immunology 6:511-519), or a phage antibody library technique (Clackson et al., Nature, 352:624-628, 1991; Marks et al., J. Mol. Biol., 222:58, 1-597, 1991). The antibodies of the present invention include complete forms, each of which consists of two full-length light chains and two full-length heavy chains, as well as functional fragments of antibody molecules. The functional fragments of antibody molecules refer to fragments retaining at least an antigen-binding function, and include Fab, F(ab'), F(ab')2 and Fv.

Antibodies that specifically recognize the α1G protein according to the present invention are not limited thereto, but may include an antibody comprising an amino acid sequence of SEQ ID NO: 2 in consistent with one embodiment of the present invention.

Further, the present invention provides a kit for pregnancy diagnosis in cattle, including the pregnancy diagnostic marker for measuring the expression level of the α1G protein or a gene encoding the same. The kit may include, but not limited to, a PCR kit, a DNA chip kit, or a protein chip kit.

The pregnancy diagnosis marker according to which is included in pregnancy diagnosis kit may include a primer, probe, or antibody capable of measuring the expression level of the α1G protein or a gene encoding the same, the definitions of which were described previously.

If the pregnancy diagnosis kit of the present invention is used in the PCR amplification procedure, the kit of the present invention may selectively include reagents required for PCR amplification, for example, buffer, DNA polymerase (for example, thermostable DNA polymerase obtained from *Thermus aquaticus* (Taq), *Thermus thermophilus* (Tth), *Thermus filiformis, Thermis flavus, Thermococcus literalis* or *Pyrococcus furiosus* (Pfu)), DNA co-polymerase, and dNTPs. If the pregnancy diagnosis kit of the present invention is applied to immunoassay, the kit of the present invention may selectively comprise a secondary antibody and a labeled substrate.

Further, the kit of the present invention may be made of a plurality of packagings or compartments including the above reagent components.

Further, the present invention provides a microarray for pregnancy diagnosis, including the pregnancy diagnostic marker for measuring the expression level of the α1G protein or a gene encoding the same.

In the microarray of the invention, the primer, probe, and antibody for measuring the expression level of the α1G protein or the gene encoding the same serve as hybridizable array elements and are immobilized on substrates. A preferable substrate includes suitable solid or semi-solid supporters, such as membrane, filter, chip, slide, wafer, fiber, magnetic or nonmagnetic bead, gel, tubing, plate, polymer, microparticle and capillary tube. The hybridizable array elements are arranged and immobilized on the substrate. Such immobilization occurs through chemical binding or covalent binding such as UV. In an example, the hybridizable array elements are bound to a glass surface modified to contain epoxy compound or aldehyde group or to a polylysine-coated surface by UV irradiation. Further, the hybridizable array elements are bound to a substrate through linkers (e.g. ethylene glycol oligomer and diamine).

If samples to be applied to the microarray of this invention are nucleic acids, they may be labeled, and hybridized with array elements on microarray. Various hybridization conditions are applicable, and for the detection and analysis of the extent of hybridization, various methods are available depending on labels used.

Further, the present invention provides a method for diagnosing pregnancy in cattle by measuring the expression level of the α1G gene or the α1G protein level. Specifically, the method may include the step of diagnosing of pregnancy in cattle by detecting the expression level of the α1G gene using the substance for measuring the level of mRNA of the α1G gene of the T-type calcium channel or the level of the α1G protein encoded from the gene. The aforementioned method for measuring the expression level of mRNA of the α1G gene or the level of the α1G protein encoded from the gene may be carried out by including a known process for isolating mRNA or protein from a biological sample by using the known art. Moreover, the substance for measuring the level of mRNA of the α1G gene or the level of the α1G protein encoded from the gene includes the aforementioned composition for pregnancy diagnosis in cattle according to the present invention.

Thus, the present invention provides a method for diagnosing pregnancy in cattle comprising detecting the level of expression of an α1G gene in the biological sample from a cow, wherein expression of an α1G gene is indicative of pregnancy of cow.

The term "biological sample", as used herein, refers to samples derived from living organisms which show a difference in the expression level of the α1G gene or the protein level from a normal control group depending on the degree of onset or progression of pregnancy, and the samples may include tissues, cells, whole blood, serum, plasma, saliva, urine, or milk, but are not limited thereto.

Preferably, the measurement of the expression level of the α1G gene involves measuring mRNA levels. Methods for measuring mRNA levels include reverse transcriptase-polymerase chain reaction (RT-PCR), real time reverse transcriptase-polymerase chain reaction, RNase protection analysis, Northern blot, DNA chip, etc, but are not limited thereto.

The measurement of the protein level can be carried out using an antibody. In this case, the α1G marker protein in a biological sample and an antibody specific thereto form binding products, i.e., antigen-antibody complexes. The amount of formed antigen-antibody complexes may be quantitatively determined by measuring the signal size of a detection label. Such a detection label may be selected from the group consisting of enzymes, fluorescent substances, ligands, luminescent substances, microparticles, redox molecules and radioactive isotopes, but the present invention is not limited to the examples. Preferably, the antibody according to the present invention may include an amino acid sequence of SEQ ID NO. 2.

Analysis methods for measuring protein levels include, but are not limited to, Western blotting, ELISA, radioimmunodiffusion, ouchterlony immunodiffusion, rocket immunoelectrophoresis, immunohistostaining, immunoprecipitation assay, complement fixation assay, FACS, and protein chip assay.

Accordingly, with the detection methods of the present invention, it is possible to determine the expression of mRNA or protein of the α1G gene in a control group and the expression of mRNA or protein of the α1G gene in cows (experimental group) with suspected pregnancy. The pregnancy of the cows in the experimental group can be predicted and diagnosed by comparing the α1G expression level of the experimental group with that of the control group.

Hereinafter, the present invention will be described in further detail with reference to the following examples. It will be obvious to a person having ordinary skill in the art that these examples are merely for illustrative purposes, and the scope of the present invention should not be construed as being limited to these examples.

REFERENCE EXAMPLE

Preparation of Protein Samples

Milk was sampled from artificially inseminated dairy cows that normally produce milk at each stage. Next, pH was lowered to 4.6 with 1N HCl in order to remove casein, the major milk protein, followed by removal of the casein by centrifugation for 20 minutes at 3200 rpm at 4° C. After that, the obtained whey (milk serum) was concentrated, then protein was quantified using the Bradford protein assay and stored frozen at −70° C. until analysis.

Example 1

Identification of α1G Protein of the Present Invention

The present inventors performed two-dimensional electrophoresis to identify proteins specifically expressed in the milk of cows during pregnancy.

<1-1> First Electrophoresis

First electrophoresis (Isoelectric focusing, IEF) was performed on 1 mg of whey (milk-serum) proteins using strip gel of pH range 6 to 9, so that the whey (milk-serum) proteins can move to the pH corresponding to their isoelectric point (pI value).

<1-2> Second Electrophoresis

After IEF, the strip was put into 10 ml of DTT equilibration buffer (1% DTT, 6M Urea, 2% SDS, 375 mM Tris pH8.8, 20% Glycerol, 2.5% Acrylamide), and then was reacted while softly shaking for 15 minutes. After discarding the DTT equilibration buffer, 10 ml of Iodoacetamide equilibration buffer (4% Iodoacetamide, 6M Urea, 2% SDS, 375 mM, Tris pH8.8, 20% Glycerol, 2.5% Acrylamide) was put in, and then subjected to equilibration while softly shaking for 15 minutes. The strip after equilibration was put into an upper layer of an immobilized 8%~16% gradient gel, and immobilized on Ettan DALT twelve Large vertical system (Amersham Bioscience) containing a SDS-PAGE running buffer (1.44% Glycine, 0.1% SDS, 0.3% Tris base), and then subjected to electrophoresis with 150 mA of electric current for 16 hours.

<1-3> Staining with Coomassie Brilliant Blue (CBB) G-250

The gel was washed with distilled water, and 1 L of an fixation solution (40% v/v methanol, 5% v/v phosphoric acid) was put in, and then fixed for 1 hour while softly shaking. Then the fixation solution was removed, and 1 L of a CBB staining solution (17% g/v Ammonium sulfate, 3% v/v phosphoric acid, 0.1% g/v Coomassie G-250, 34% v/v methanol) was put in, and stained for at least 12 hours while softly shaking. The stained gel was loaded a destaining solution (1% acetic acid, 0.02% sodium azide) to destain the gel for at least 12 hours.

<1-4> Scanning and Image Analysis

Figure 1A:
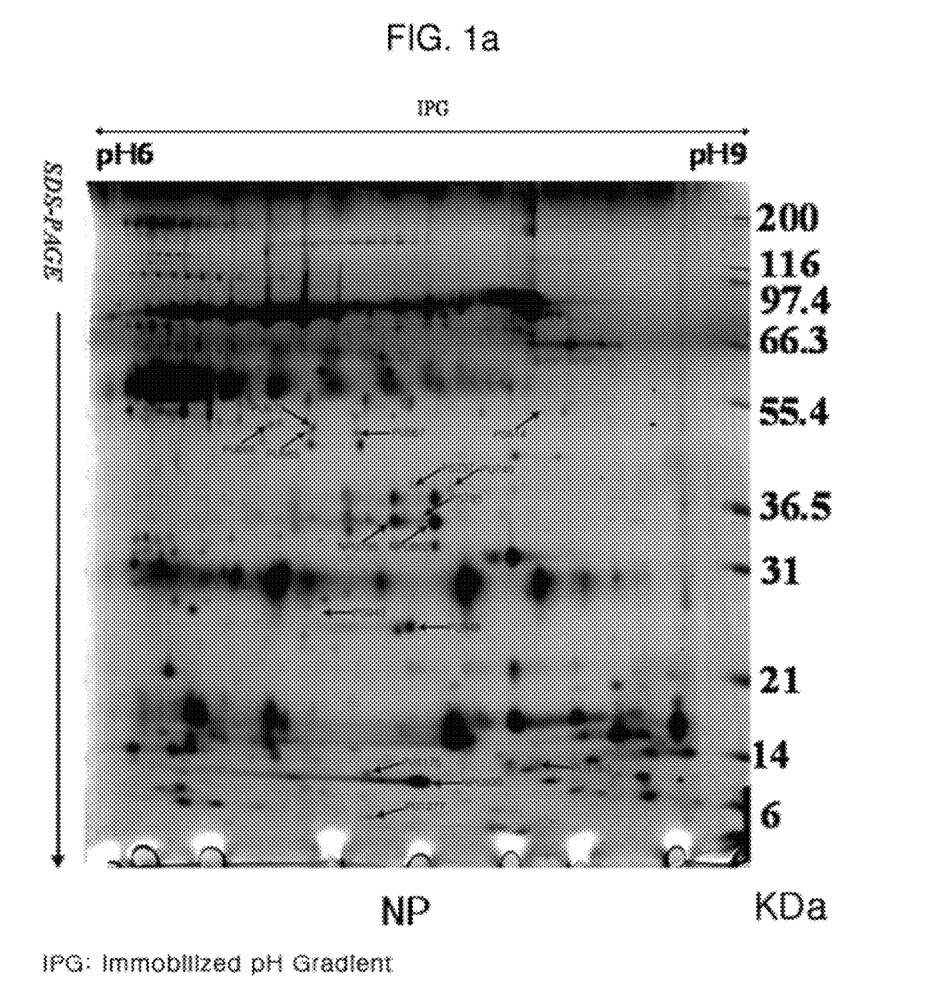
FIGS. 1a and 1b are images of whey proteins in pregnant and nonpregnant cows, the whey proteins being subjected to 2-D electrophoresis using strips of pH 6-9 and then stained with Coomassie, where an average of 700 protein spots were observed in gel by image analysis using Imagemaster (P: milk samples from cows at 30 days of pregnancy, NP: milk samples from nonpregnant cows)
Figure 1B:
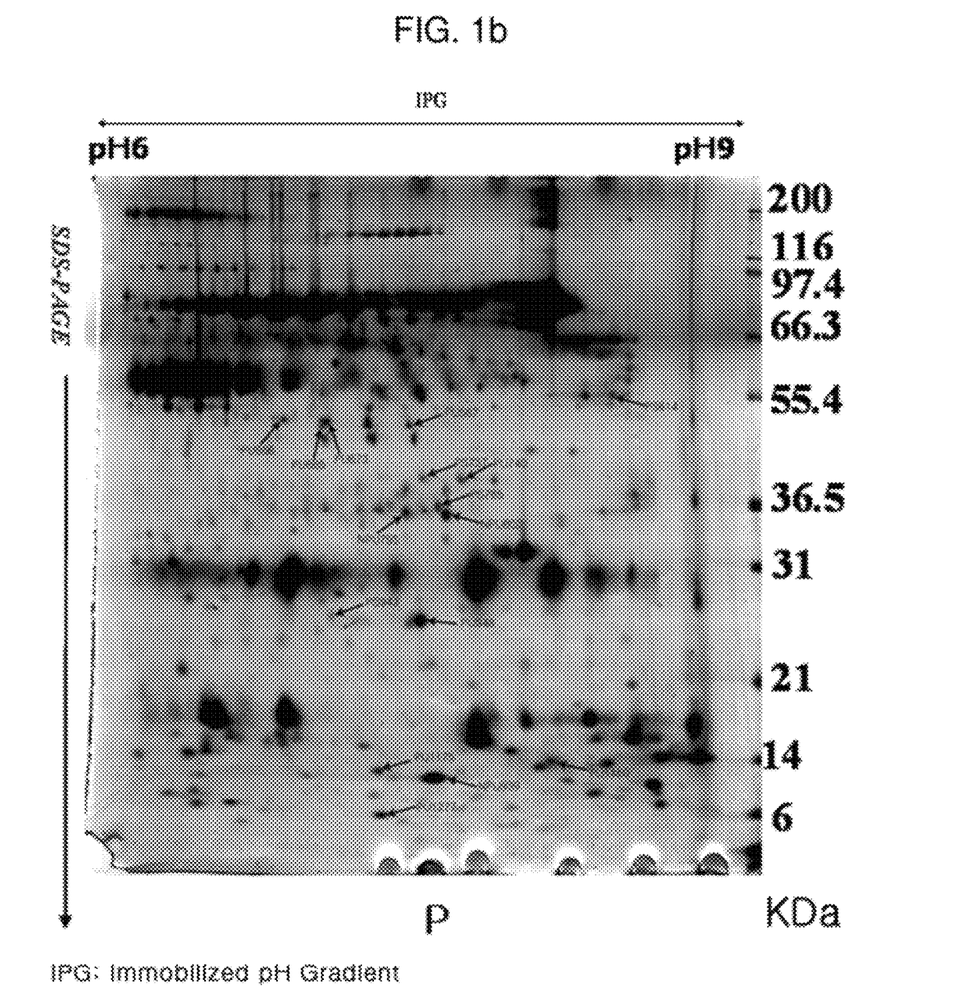

The gel images were scanned by a scanner, and then analyzed with ImageMaster 2D platinum software version 5.0 program to obtain statistical data and analyze protein spots showing differences in expression. As shown in FIGS. 1a and 1b, the result showed that about 700 distinguishable protein spots appeared throughout the entire gel and therefore normal second-dimensional electrophoresis was carried out.

<1-5> α1G Protein Identification using MALDI-TOF and ESI-MS/MS

After image analysis, the protein spots showing differences were sliced, put into 1.5 ml of microtube, 120 µl of a washing buffer (50% v/v acetonitrile, 25 mM ammonium carbonate, pH7.8) was added, destaining was repeated until blue color of CBB disappears, and then lyophilization was performed on the destained gel spot slices (pieces) by using Vacuum centrifuge.

5 µl of a trypsin buffer (0.02/µg trypsin/ml, 25 mM ammonium carbonate) was put in the dried gel slice, rehydrated for 1 hour, and 25 mM ammonium bicarbonate buffer was added to the gel silce, and reaction was performed for at least 12 hours at 37° C. 5 µl of an extraction buffer (50% Acetonitrile, 0.1% Trifluoro acetic acid (TFA), third distilled water) was put in, and subjected to sonication for 30 minutes, and then 1 µl of sample was taken, to which 1 µl of a matrix solution α-cyano-4-hydroxycinnamic acid 10 mg/g in 50% v/v acetonitrile, 0.1% TFA) was added and mixed, plated on 384-well plate (Perseptive Biosystems, Framingham, Mass., USA), and dried for 30 minutes to prepare a sample.

The peptide in 96-well plate was analyzed with MALDI-TOF (Perseptive Biosystems, Framingham, Mass., USA) to measure the molecular weight of the peptide liberated by trypsin. The molecular weight data for the measured peptide was searched in a website database (http://prowl.rockefeller.edu/prowl-cgi/profound.exe) to identify a protein (see FIG. 3).

Figure 2:
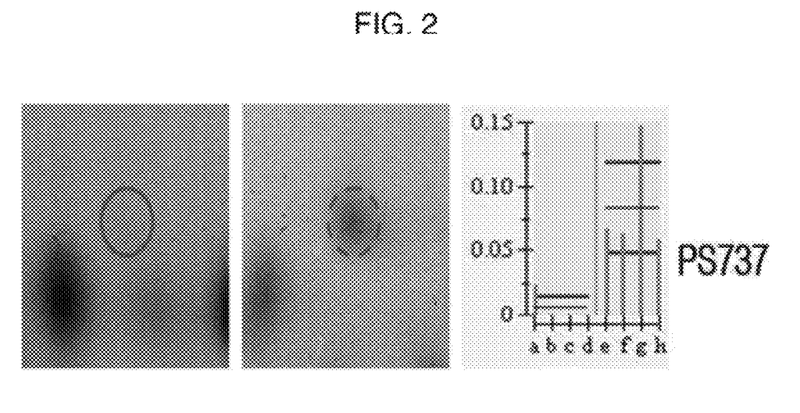
FIG. 2 is a magnified image of spot portions expressed specifically to pregnancy in an image obtained after 2-D electrophoresis and a chart showing statistical differences between pregnant and nonpregnant cows by analysis using Imagemaster (P: milk samples from cows at 30 days of pregnancy, NP: milk samples from nonpregnant cows)

Consequently, the present inventors analyzed the protein spots expressed specifically to pregnancy by second-dimensional electrophoresis, and detected spots consistently expressed in each of the repeated samples, and therefore identified α1G proteins whose expression is higher specifically in the milk of pregnant cows than in the milk of nonpregnant cows (see FIG. 2).

Example 2

Production of Antibody of α1G Protein of Present Invention

The present inventors intended to produce an actual antibody for effectively detecting the α1G protein after confirming the presence of the α1G protein expressed specifically to pregnancy in the milk from pregnant cows through the aforementioned examples.

A region with low probability of generation of α-helix and β-sheet was chosen from the α1G protein by DNAATAR program, and sequences with less similarity were selected from NCBI by the homology analysis of peptide sequences, thereby producing an antibody having high surface exposure, high antigenicity, and high flexibility and being specific to pregnancy.

The C- to N-terms of the peptide were sequentially synthesized by solid-phase synthesis using Fmoc chemistry. After the synthesis was completed, the peptide was treated with greater than 90% TFA, then analyzed by high-performance liquid chromatography (HPLC), and the mass of the peptide was determined. The carrier protein was activated with a linker (KLH was activated with GMBS linker, and OVA was activated with MBS linker), the peptide was dissolved in distilled water or a DMSO solution, the carrier protein and the peptide solution were mixed together, 1/10 vol of 50 mM EdtA (NaPi[pH7.5] solution) was added and reacted for 2 hours at room temperature, conjugation was detected using Ellman's reagent and SDS-PAGE, and then the peptide was desalted.

A 1.8 kg New Zealand White rabbit was prepared (acclimated to the animal facility about 1 week before immunization), 400 µg of conjugate/500 µl of PBS and 500 µl of Freund's complete adjuvant were mixed to prepare an emulsion, and the rabbit was subcutaneously injected with the emulsion. Three weeks later, the same amount of antigen and Freund's incomplete adjuvant as used during the first injection were mixed to carry out first boosting. After 1 week later, a small amount of serum was collected to perform ELISA and obtain test serum. Three weeks after the first boosting, second boosting was carried out using the same amount of antigen and Freund's incomplete adjuvant. After 1 week later, a small amount of serum was collected to perform ELISA and obtain test serum. Three weeks after the second boosting, third boosting was carried out using the same amount of antigen and Freund's incomplete adjuvant. After 1 week later, exsanguination was performed to obtain serum.

Figure 3:
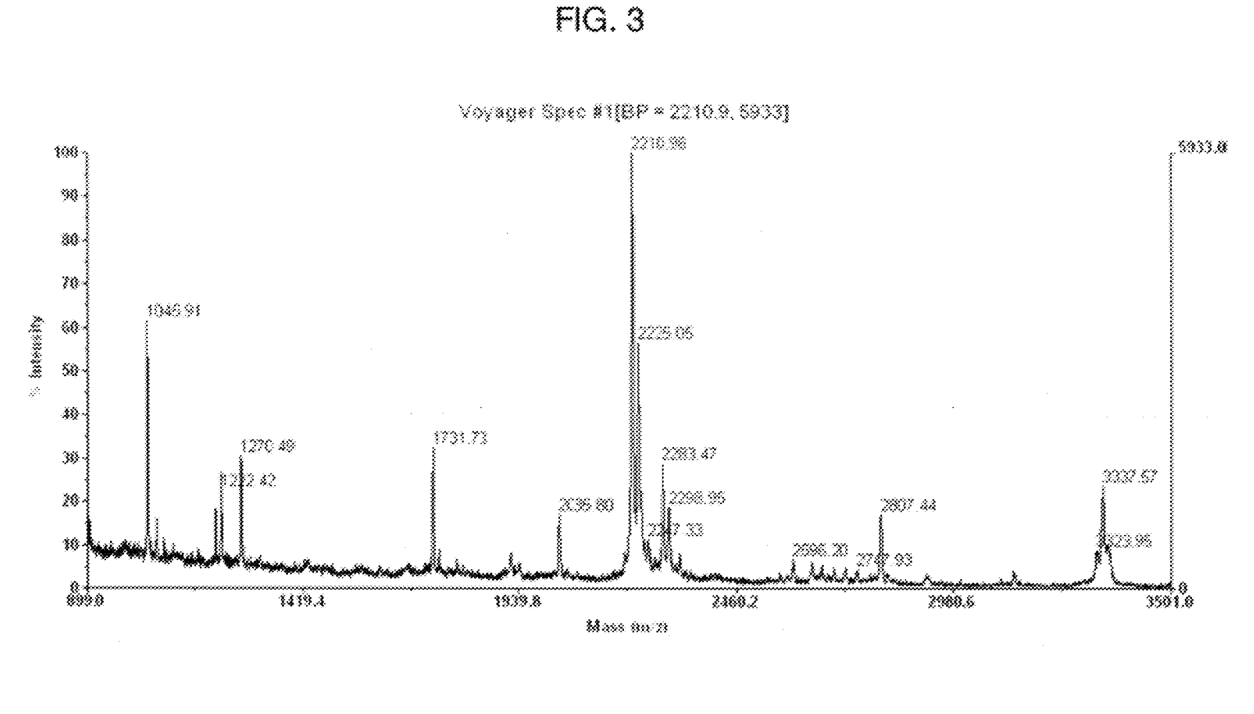
FIG. 3 is a graphic image of α1G protein obtained by using MALDI-TOF Mass Spectrometer.

As a result, the present inventors produced an antibody of α1G subunit of the T-type calcium channel having an amino acid sequence of sequence list 2(HGDLRDPHSRRRRSL) from among proteins highly expressed in the milk of pregnant cows (see FIG. 3).

Example 3

Analysis of Pregnancy Diagnosis Using α1G Antibody of Present Invention

To analyze whether the antibody produced in the above examples can precisely determine the pregnancy of cows, the present inventors analyzed changes occurring during pregnancy by performing Western blot of milk samples from pregnant cows and nonpregnant cows with the produced antibody.

30 µg of milk protein samples were loaded into 12% SDS-PAGE gel to perform electrophoresis. Following the electrophoresis of SDS-PAGE, the proteins on the gel phase were transferred to PVDF membrane. A TBS-T blocking solution (25 mM Tris-base, 0.8% NaCl, 0.002% KCl, 5% non fat milk power, 0.1% Tween-20, pH 7.4) was added to this membrane, and then stirred for 2 to 3 hours at room temperature. The PVDF membrane was washed with a TBS-T buffer (25 mM Tris-base, 0.8% NaCl, 0.002% KCl, 0.1% Tween-20, pH 7.4) twice, each time for 10 minutes, and then a polyclonal anti-α1G antibody (1:5000) was put into the TBS-T buffer and incubated for 1 hour. Again, the membrane was washed with the TBS-T buffer twice, each time for 15 minutes, and then a second antibody (rabbit IgG 1:1000) was put into the TBS-T buffer and incubated for 1 hour. After the incubation, the membrane was washed with the TBS-T buffer three times, each time for 10 minutes, and then developed with an ECL kit.

Figure 4A:
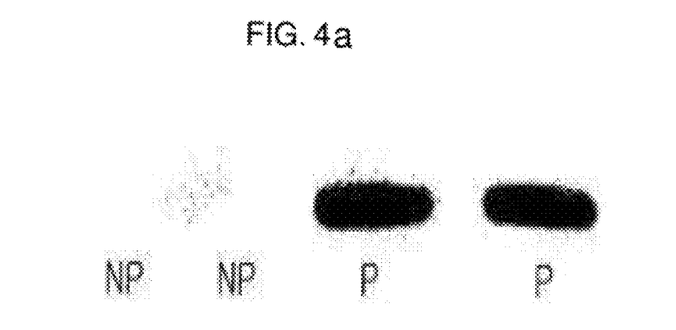
FIG. 4a shows a result of examining pregnant and nonpregnant samples by using an antibody synthesized according to the amino acid sequence of α1G protein (NP: nonpregnant, P: pregnant)
Figure 4B:
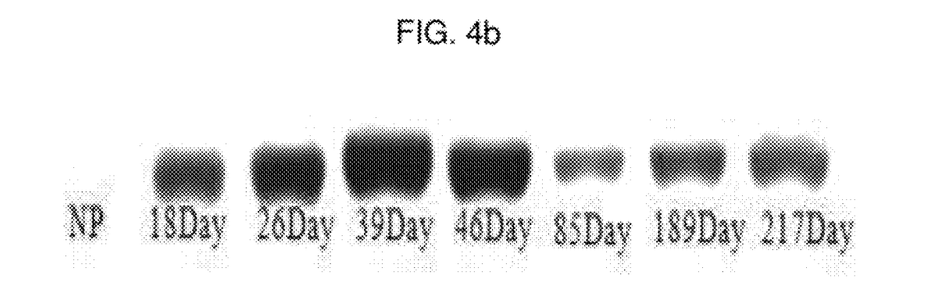
FIG. 4b shows changes in pregnancy-specific proteins in milk samples according to the number of days of pregnancy which were detected using the antibody.

As a result, the analysis showed that the antibodies were highly expressed only in the samples from pregnant cows (see FIG. 4a). Moreover, as a result of performing Western blot of the milk samples for each period of pregnancy with these antibodies, the present inventors confirmed that the expression of the antibodies in the serum during an early stage of pregnancy was low and increased after around 10 days of pregnancy, and also confirmed that the expression tends to increase in the early stage of pregnancy and decrease in the middle and later stages of pregnancy (see FIG. 4b).

Although there are differences in expression level between each period, it can be seen that α1G protein expression tends to increase remarkably throughout whole period (all stages) of pregnancy.

From these results, the present inventors have concluded that the α1G protein is expressed specifically in pregnant cows throughout whole period of pregnancy, including an early stage of pregnancy, and also concluded that the antibody produced in the present invention can be used as excellent means for diagnosing pregnancy.

Hitherto, the present invention has been described with reference to preferred examples. It shall be understood by a person of ordinary skill in the art to which the present invention pertains that the present invention can be embodied in modified forms without departing from the essential features of the present invention. Therefore, the disclosed embodiment shall be understood in a descriptive perspective, not a restrictive perspective. The scope of the present invention is disclosed in the appended claims, not in the above description, and it shall be interpreted that all differences within the equivalent scope are included in the present invention.

What is claimed is:

1. A composition comprising an antibody that binds specifically to the amino acid sequence of SEQ ID NO:2.

\* \* \* \* \*

SEQUENCE LISTING

```
<160> NUMBER OF SEQ ID NOS: 2

<210> SEQ ID NO 1
<211> LENGTH: 342
<212> TYPE: PRT
<213> ORGANISM: Artificial Sequence
<220> FEATURE:
<223> OTHER INFORMATION: alpha1G protein

<400> SEQUENCE: 1

Ser Glu Thr Lys Gln Arg Glu Ser Gln Leu Met Arg Glu Gln Arg Val
1               5                   10                  15

Arg Phe Leu Ser Asn Ala Ser Thr Leu Ala Ser Phe Ser Glu Pro Gly
                20                  25                  30

Ser Cys Tyr Glu Glu Leu Leu Lys Tyr Leu Val Tyr Ile Leu Arg Lys
            35                  40                  45

Ala Ala Arg Arg Leu Ala Gln Val Ser Arg Ala Ala Gly Val Arg Val
        50                  55                  60

Gly Leu Leu Ser Ser Pro Ala Pro Arg Gly Gly Gln Glu Pro Gln Pro
65                  70                  75                  80

Ser Gly Gly Cys Pro Arg Pro His Arg Arg Pro Ser Val His His Leu
                85                  90                  95

Met His His His His Pro His Tyr His Leu Gly Asn Gly Thr Leu
                100                 105                 110

Arg Ala Pro Arg Pro Ser Pro Gln Ile Gln Asp Arg Asp Ala Ser Gly
            115                 120                 125

Ser Arg Arg Leu Val Leu Pro Pro Ser Thr Pro Ala Leu Ser Arg
        130                 135                 140

Gly Pro Pro Gly Gly Ala Glu Ala Val His Ser Phe Tyr His Ala Asp
145                 150                 155                 160

Cys His Leu Glu Pro Val Arg Cys Gln Ala Pro Pro Pro Arg Ser Pro
                165                 170                 175

Ser Glu Ala Ser Gly Arg Thr Val Asp Ser Gly Lys Val Tyr Pro Thr
            180                 185                 190

Val His Thr Ser Pro Pro Pro Glu Met Leu Lys Glu Lys Ala Leu Met
        195                 200                 205

Glu Val Ala Pro Ala Ser Gly Pro Thr Thr Leu Thr Gly Leu Asn Ile
    210                 215                 220

Pro Pro Arg Pro Tyr Ser Ser Met His Lys Leu Leu Glu Thr Gln Ser
225                 230                 235                 240
```

```
Thr Gly Ala Cys Gln Ser Ser Cys Lys Ile Ser Ser Pro Cys Leu Arg
                245                 250                 255

Ala Ala Ser Gly Ala Cys Gly Pro Asp Ser Cys Pro Tyr Cys Ala Arg
            260                 265                 270

Thr Gly Ala Gly Glu Val Gly Leu Thr Gly His Glu Met Pro Asp Ser
        275                 280                 285

Asp Ser Glu Ala Val Tyr Glu Phe Thr Gln Ala Gln His Gly Asp
    290                 295                 300

Leu Arg Asp Pro His Ser Arg Arg Arg Ser Leu Gly Leu Asp Val
305                 310                 315                 320

Glu Pro Asn Ser Val Leu Ala Phe Trp Arg Leu Ile Cys Asp Thr Phe
                325                 330                 335

Arg Lys Ile Val Asp Ser
            340

<210> SEQ ID NO 2
<211> LENGTH: 15
<212> TYPE: PRT
<213> ORGANISM: Artificial Sequence
<220> FEATURE:
<223> OTHER INFORMATION: antibody of alpha1G

<400> SEQUENCE: 2

His Gly Asp Leu Arg Asp Pro His Ser Arg Arg Arg Ser Leu
1               5                   10                  15
```